(12) United States Patent
Lee

(10) Patent No.: US 8,111,161 B2
(45) Date of Patent: Feb. 7, 2012

(54) METHODS, SYSTEMS AND/OR APPARATUS RELATING TO TURBINE BLADE MONITORING

(75) Inventor: Dongjai Lee, Greer, SC (US)

(73) Assignee: General Electric Company, Schenectady, NY (US)

(*) Notice: Subject to any disclaimer, the term of this patent is extended or adjusted under 35 U.S.C. 154(b) by 293 days.

(21) Appl. No.: 12/394,142

(22) Filed: Feb. 27, 2009

(65) Prior Publication Data

US 2010/0219942 A1    Sep. 2, 2010

(51) Int. Cl.
*G08B 13/14* (2006.01)
(52) U.S. Cl. .................. 340/572.1; 340/539.1; 340/10.1
(58) Field of Classification Search ............... 340/572.1, 340/679, 665, 686.3; 290/44, 55; 324/636
See application file for complete search history.

(56) References Cited

U.S. PATENT DOCUMENTS

| | | | |
|---|---|---|---|
| 7,259,552 B2* | 8/2007 | Twerdochlib | 324/207.16 |
| 7,360,996 B2 | 4/2008 | Driver | |
| 7,400,054 B2* | 7/2008 | Wesselink | 290/44 |
| 7,849,752 B2* | 12/2010 | Gregory et al. | 73/773 |
| 2004/0113790 A1 | 6/2004 | Hamel et al. | |
| 2005/0287386 A1 | 12/2005 | Sabol et al. | |
| 2006/0018361 A1 | 1/2006 | Hardwicke et al. | |
| 2007/0108770 A1* | 5/2007 | Riesberg | 290/44 |
| 2007/0159346 A1 | 7/2007 | Wesselink | |
| 2009/0277266 A1* | 11/2009 | Wang et al. | 73/514.01 |

OTHER PUBLICATIONS

European Patent Office Search Report, Jun. 21, 2010.

* cited by examiner

*Primary Examiner* — Toan N Pham
(74) *Attorney, Agent, or Firm* — Mark E. Henderson; Ernest G. Cusick; Frank A. Landgraff

(57) ABSTRACT

A method of monitoring a rotor blade of a turbine engine that includes a plurality of blades mounted to a rotor shaft, comprising: a) securing a RFID tag that includes an antenna to at least one of the rotor blades; b) securing a RFID reader on a stationary surface on the turbine engine in operational proximity to the RFID tag; and c) during operation of the turbine engine, monitoring the RFID tag with the RFID reader.

18 Claims, 4 Drawing Sheets

METHODS, SYSTEMS AND/OR APPARATUS RELATING TO TURBINE BLADE MONITORING

BACKGROUND OF THE INVENTION

This present application relates generally to methods, systems, and/or apparatus for improving the efficiency and/or operation of turbine engines, which, as used herein and unless specifically stated otherwise, is meant to include all types of turbine or rotary engines, including gas turbine engines, aircraft engines, steam turbine engines, and others. More specifically, but not by way of limitation, the present application relates to methods, systems, and/or apparatus pertaining to improved turbine blade diagnostics, including the usage of RFID technology to transmit status information that may be used in diagnostic applications.

A gas turbine engine typically includes a compressor, a combustor, and a turbine. The compressor and turbine generally include rows of blades that are axially stacked in stages. Each stage includes a row of circumferentially-spaced stator blades, which are fixed, and a row of rotor blades, which rotate about a central axis or shaft. In operation, generally, the compressor rotor blades rotate about the shaft, and, acting in concert with the stator blades, compress a flow of air. The supply of compressed air then is used in the combustor to combust a supply of fuel. Then, the resulting flow of hot expanding gases from the combustion, i.e., the working fluid, is expanded through the turbine section of the engine. The flow of working fluid through the turbine induces the rotor blades to rotate. The rotor blades are connected to a central shaft such that the rotation of the rotor blades rotates the shaft.

In this manner, the energy contained in the fuel is converted into the mechanical energy of the rotating shaft, which, for example, may be used to rotate the rotor blades of the compressor, such that the supply of compressed air needed for combustion is produced, and the coils of a generator, such that electrical power is generated. During operation, because of the extreme temperatures of the hot-gas path, the velocity of the working fluid, and the rotational velocity of the engine, turbine blades, which, as described, generally include both the rotating rotor blades and the fixed, circumferentially-spaced stator blades, become highly stressed with extreme mechanical and thermal loads.

Given these conditions, it is important for compressor and turbine rotor blade health to be monitored closely. As one of ordinary skill in the art will appreciate, a blade failure may cause catastrophic and expensive damage to a turbine engine. Generally, many such blade failures may be predicted and, thereby, avoided if data concerning strain levels and/or crack formation/propagation in certain highly stressed areas on the blade is accurately collected and monitored. Generally, though, such data is either impossible or prohibitively expensive to collect and, when it is collected by conventional means, the data is unreliable. For example, tip timing is a conventional method that measures blade vibration frequency. It is believed that the presence of a crack alters the operating vibration frequency of a blade and, thus, may be used to warn of a compromised blade. However, results from this method have proved unreliable in many applications. Of course, another method is to shut down the turbine engine and the visually inspect the blades. This type of inspection, though, provides no information about the stress occurring during operation, is also prone to unreliability, and is very expensive because of both the required labor and the need to shut down the engine. As a result, there is a continuing need for methods, systems, and/or apparatus pertaining to improved turbine blade monitoring and diagnostics and, particularly, accurate ways of monitoring and accessing rotor blade health while the turbine is operating.

BRIEF DESCRIPTION OF THE INVENTION

The present application thus describes a method of monitoring a rotor blade of a turbine engine that includes a plurality of blades mounted to a rotor shaft, comprising: a) securing a RFID tag that includes an antenna to at least one of the rotor blades; b) securing a RFID reader on a stationary surface on the turbine engine in operational proximity to the RFID tag; and c) during operation of the turbine engine, monitoring the RFID tag with the RFID reader.

The present application further describes a turbine engine comprising: a plurality of rotor blades mounted to a shaft; a RFID tag that includes an antenna secured to at least a plurality of the rotor blades; a RFID reader secured to a stationary surface on the turbine engine in operational proximity to the RFID tag; wherein the RFID reader is configured to monitor the RFID tags as the RFID tags pass the RFID reader during operation.

These and other features of the present application will become apparent upon review of the following detailed description of the preferred embodiments when taken in conjunction with the drawings and the appended claims.

BRIEF DESCRIPTION OF THE DRAWINGS

These and other objects and advantages of this invention will be more completely understood and appreciated by careful study of the following more detailed description of exemplary embodiments of the invention taken in conjunction with the accompanying drawings, in which.

DETAILED DESCRIPTION OF THE INVENTION

Figure 1:
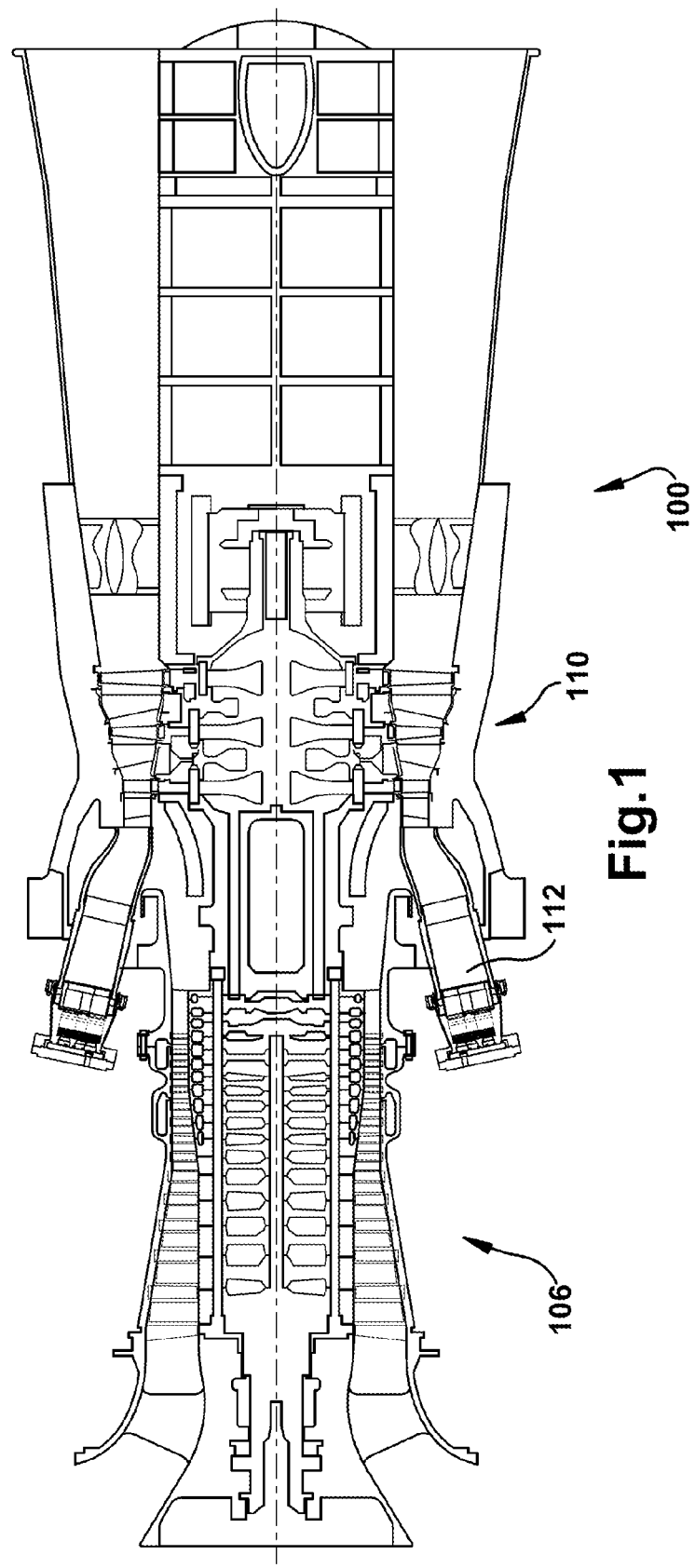
FIG. 1 is a schematic representation of an exemplary gas turbine engine in which embodiments of the present application may be used.

Radio frequency identification ("RFID") tagging is a known method of identification in certain arts. In particular, a reader of a conventional RFID system produces and emits an electromagnetic interrogation field at a specific frequency when excited by connected electronic drive circuitry. The RFID tag or device typically includes a semiconductor chip having RF circuits, logic, and memory, as well as an antenna. The device functions in response to the coded radio frequency (RF) signal. If the device is positioned within the interrogation field for a sufficient time, the RFID inlay will become stimulated and transmit a uniquely coded signal that is received by the reader or a separate receiving antenna. The RF carrier signal is demodulated to recover information stored in the RFID device. Various RFID structures, circuits, and programming protocols are known in the art. Examples are described in U.S. Pat. No. 5,682,143 (Brady et al.) and U.S. Pat. No. 5,444,223 (Blama), both of which are incorporated herein by reference.

Although RFID devices or tags are not yet as prevalent as other identification means, RFID devices are gaining in popularity in various applications. These include railway boxcar and tractor-trailer identification schemes, fare cards for buses and subways, animal identification, employee and security badges, and in automatic highway toll systems. In an automatic highway toll system, for example EZ Pass, drivers mount an RFID device on the front vehicle windshield. The RFID device is preprogrammed with driver information, such as account status, vehicle information, etc. As the vehicle passes through a toll, a base transmitter at the tollbooth emits a signal which is reflected by the RFID device. If the driver's account is satisfactory, a green light activates; indicating the driver is free to pass through the toll.

Electronic RFID devices are commercially available and do not per se embody the invention. Early RFID systems were developed utilizing relatively large packages, which limited the products on which they could be used. More recently, RFID devices have been made smaller so that they may be readily incorporated in tags or labels and their use can be more widespread. Such electronic devices are characterized in that they are thin, flat and generally flexible devices.

As one of ordinary skill in the art will appreciate, RFID tags may be characterized as "active" or "passive". Active RFID tags use internal batteries to power their circuits. An active tag also uses its battery to broadcast radio waves to a reader. Active tags generally broadcast high frequencies from 850 to 950 MHz that can be read 100 feet or more away. Passive RFID tags rely entirely on the reader as their power source. These tags may be read up to 20 feet away, and they have lower production costs. In general, either tag works in the same way: 1) data stored within an RFID tag's microchip waits to be read; 2) the tag's antenna receives electromagnetic energy from a RFID reader's antenna; 3) using power from its internal battery—in the case of active tags—or power harvested from the reader's electromagnetic field (in the case of passive tags), the tag sends radio waves back to the reader; and 4) the reader picks up the tag's radio waves and interprets the frequencies as meaningful data.

The invention of the present application proposes to integrate RFID transponder technology into the rotating blades of a turbine engine, such as a gas turbine, steam turbine or aircraft engine, to make it possible to transfer data wirelessly from the rotating blades to a stationary position near the rotating blades, such as a location on the surrounding turbine casing without any requirement for power input to the transponder disposed on the blade.

Referring now to the figures, FIG. 1 illustrates a schematic representation of a gas turbine engine 100. In general, gas turbine engines operate by extracting energy from a pressurized flow of hot gas that is produced by the combustion of a fuel in a stream of compressed air. As illustrated in FIG. 1, gas turbine engine 100 may be configured with an axial compressor 106 that is mechanically coupled by a common shaft or rotor to a downstream turbine section or turbine 110, and a combustor 112 positioned between the compressor 106 and the turbine 110. Note that the following invention may be used in all types of turbine engines, including gas turbine engines, steam turbine engines, aircraft engines, and others. Hereinafter, the invention will be described in relation to a gas turbine engine. This description is exemplary only and not intended to be limiting in any way.

Figure 2:
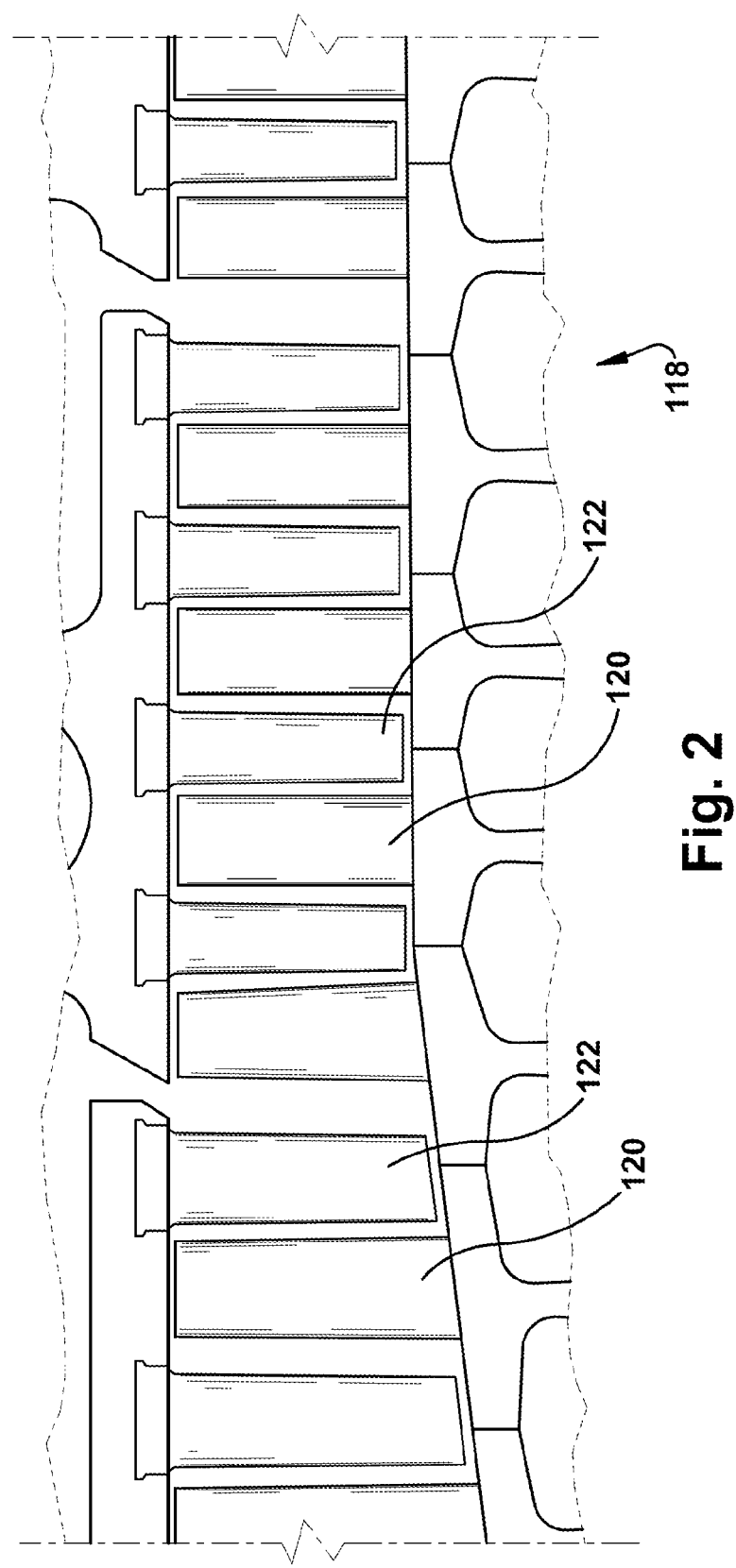
FIG. 2 is a sectional view of a compressor in a gas turbine engine in which embodiments of the present application may be used.

FIG. 2 illustrates a view of an exemplary multi-staged axial compressor 118 that may be used in a gas turbine engine. As shown, the compressor 118 may include a plurality of stages. Each stage may include a row of compressor rotor blades 120 followed by a row of compressor stator blades 122. Thus, a first stage may include a row of compressor rotor blades 120, which rotate about a central shaft, followed by a row of compressor stator blades 122, which remain stationary during operation. The compressor stator blades 122 generally are circumferentially spaced one from the other and fixed about the axis of rotation. The compressor rotor blades 120 are circumferentially spaced and attached to the shaft such that when the shaft rotates during operation, the compressor rotor blades 120 rotate about it. As one of ordinary skill in the art will appreciate, the compressor rotor blades 120 are configured such that, when spun about the shaft, they impart kinetic energy to the air or working fluid flowing through the compressor 118. The compressor 118 may have many other stages beyond the stages that are illustrated in FIG. 2. Additional stages may include a plurality of circumferential spaced compressor rotor blades 120 followed by a plurality of circumferentially spaced compressor stator blades 122.

Figure 3:
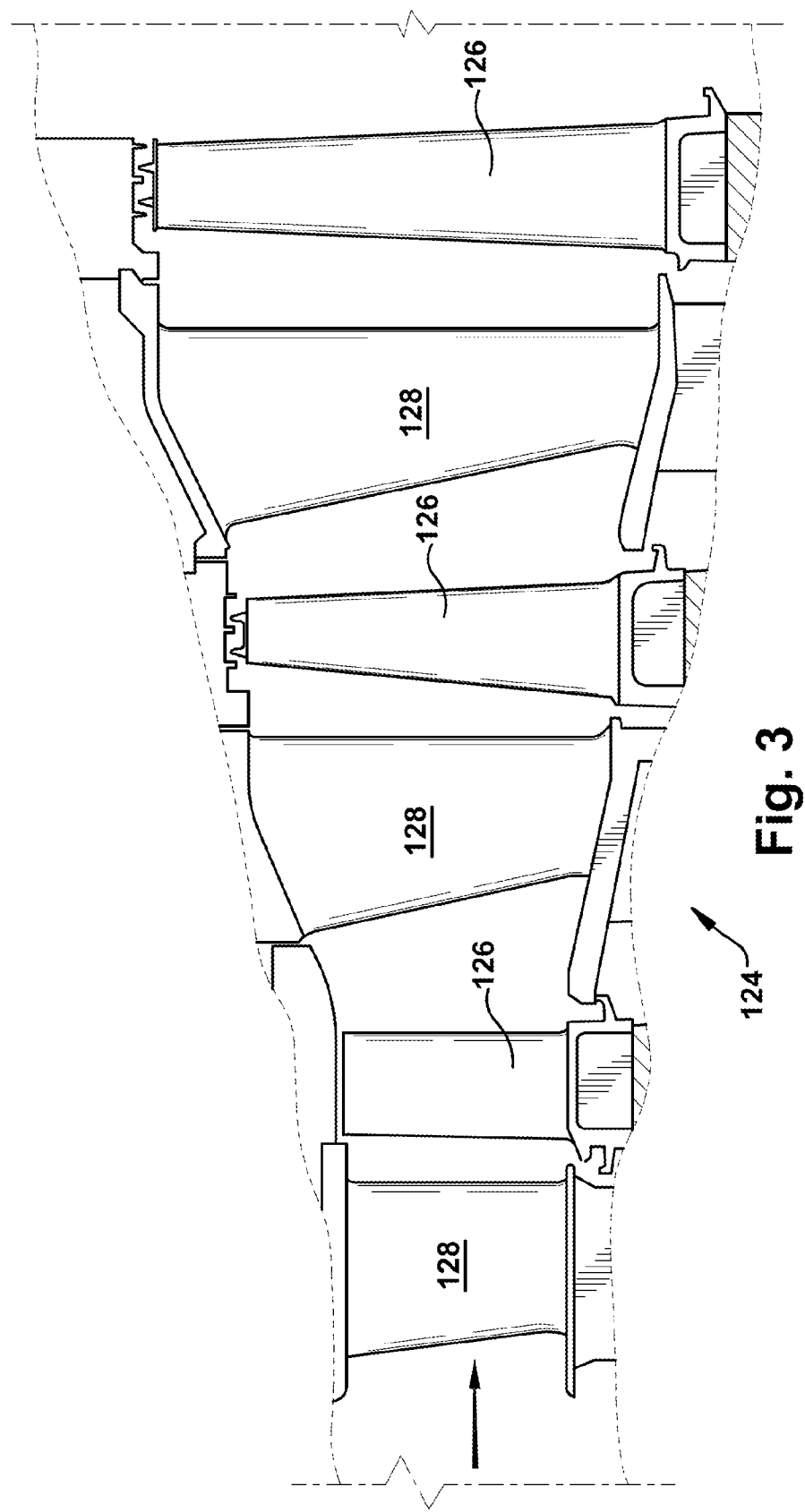
FIG. 3 is a sectional view of a turbine in a gas turbine engine in which embodiments of the present application may be used.

FIG. 3 illustrates a partial view of an exemplary turbine section or turbine 124 that may be used in the gas turbine engine. The turbine 124 also may include a plurality of stages. Three exemplary stages are illustrated, but more or less stages may be present in the turbine 124. A first stage includes a plurality of turbine buckets or turbine rotor blades 126, which rotate about the shaft during operation, and a plurality of nozzles or turbine stator blades 128, which remain stationary during operation. The turbine stator blades 128 generally are circumferentially spaced one from the other and fixed about the axis of rotation. The turbine rotor blades 126 may be mounted on a turbine wheel (not shown) for rotation about the shaft (not shown). A second stage of the turbine 124 also is illustrated. The second stage similarly includes a plurality of circumferentially spaced turbine stator blades 128 followed by a plurality of circumferentially spaced turbine rotor blades 126, which are also mounted on a turbine wheel for rotation. A third stage is illustrated, and similarly includes a plurality of turbine stator blades 128 and turbine rotor blades 126. It will be appreciated that the turbine stator blades 128 and turbine rotor blades 126 lie in the hot gas path of the turbine 124. The direction of flow of the hot gases through the hot gas path is indicated by the arrow. As one of ordinary skill in the art will appreciate, the turbine 124 may have many other stages beyond the stages that are illustrated in FIG. 3. Each additional stage may include a row of turbine stator blades 128 followed by a row of turbine rotor blades 126.

Note that as used herein, reference, without further specificity, to "rotor blades" is a reference to the rotating blades of either the compressor 118 or the turbine 124, which include both compressor rotor blades 120 and turbine rotor blades 126. Reference, without further specificity, to "stator blades" is a reference to the stationary blades of either the compressor 118 or the turbine 124, which include both compressor stator blades 122 and turbine stator blades 128. The term "blades" will be used herein to refer to either type of blade. Thus, without further specificity, the term "blades" is inclusive to all type of turbine engine blades, including compressor rotor blades 120, compressor stator blades 122, turbine rotor blades 126, and turbine stator blades 128.

In use, the rotation of compressor rotor blades 120 within the axial compressor 118 may compress a flow of air. In the combustor 112, energy may be released when the compressed air is mixed with a fuel and ignited. The resulting flow of hot gases from the combustor 112 then may be directed over the turbine rotor blades 126, which may induce the rotation of the turbine rotor blades 126 about the shaft, thus transforming the energy of the hot flow of gases into the mechanical energy of the rotating blades and, because of the connection between the rotor blades in the shaft, the rotating shaft. The mechanical energy of the shaft may then be used to drive the rotation of the compressor rotor blades 120, such that the necessary supply of compressed air is produced, and also, for example, a generator to produce electricity.

As discussed above, it is important for compressor and turbine rotor blade health to be monitored closely as the failure of one of the blades may cause catastrophic damage to the turbine engine. Blade failures may be predicted and, thereby, avoided if data concerning strain levels and/or crack formation/propagation in certain highly stressed areas on the blade is accurately collected and monitored. Generally, though, such data is either impossible or prohibitively expensive to collect and, when it is collected by conventional means, the data is unreliable. As a result, there is a continuing need for methods, systems, and/or apparatus pertaining to improved turbine blade monitoring and diagnostics and, particularly, accurate ways of accessing rotor blade health while the turbine is operating.

Figure 4:
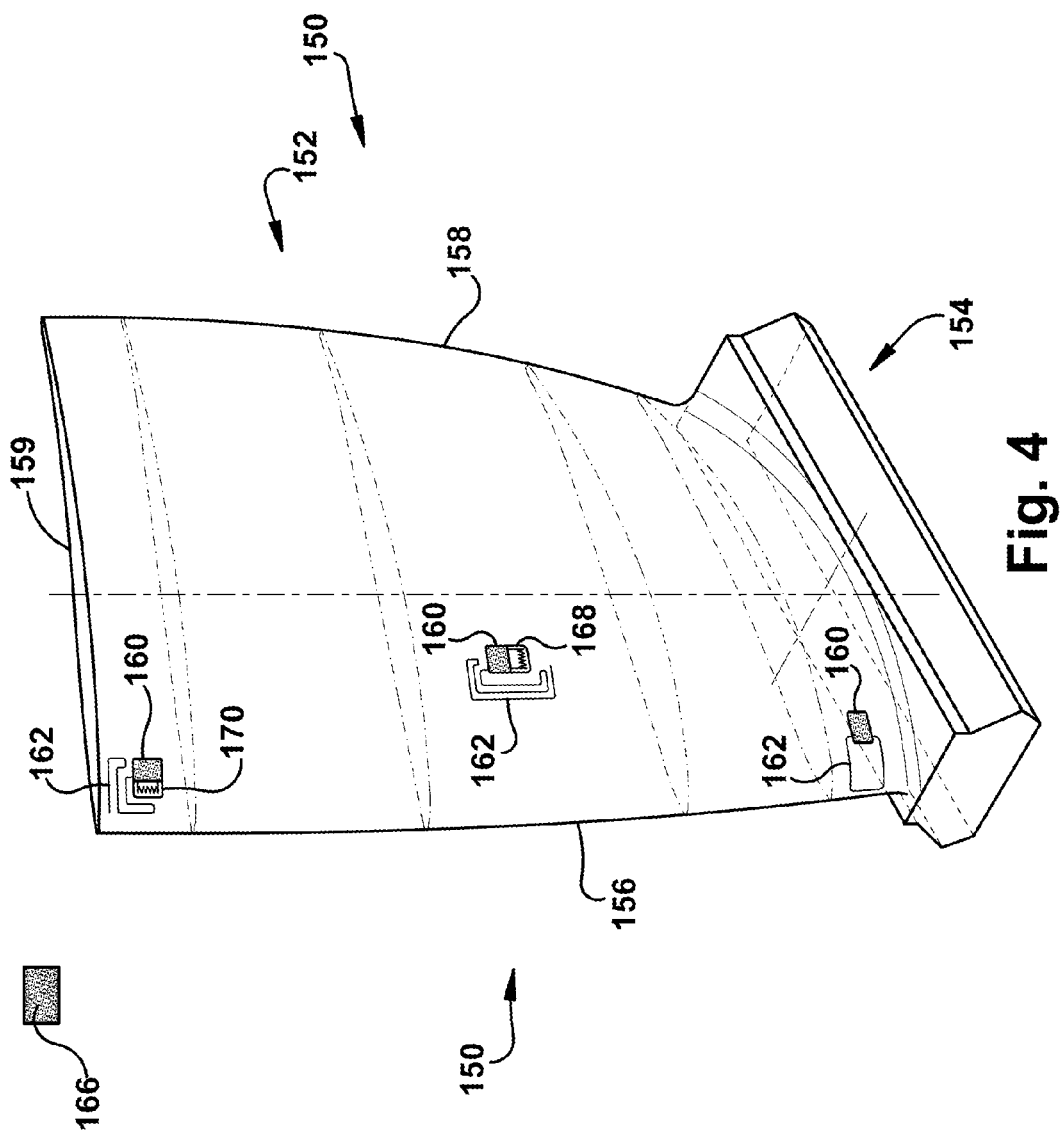
FIG. 4 is a schematic representation of an exemplary compressor rotor blade showing the placement of RFID tags and the relative location of a reader/receiver according to an exemplary embodiment of the present application.

By way of example, FIG. 4 schematically illustrates a compressor rotor blade 150. As one of ordinary skill in the art will appreciate, the compressor rotor blade 150 generally includes an airfoil 152 that extends radially from a root 154, which it generally is integral therewith. The airfoil 152 generally includes a concave pressure sidewall or pressure side and a circumferentially or laterally opposite, convex suction sidewall or suction side. Both the pressure sidewall and the suction sidewall extend axially between a leading edge 156 and a trailing edge 158. The pressure sidewall and the suction sidewall further extend in the radial direction between the root 154 and a radially outer blade tip 159.

According to example embodiments of the invention, an RFID tag or tags 160, may be bonded per conventional means to one or more location on the rotor blade 150. As shown in FIG. 4 (though not depicted to scale), a tag 160 may be applied to: 1) the leading edge 156 of the airfoil 152 at an inner radial location, i.e., near the root 154; 2) the approximate mid-area of the suction side of the airfoil 152; and/or 3) near the outer radial edge of the suction side of the airfoil 152 near the leading edge 156. These preferred locations are exemplary, as there are several locations on a rotor blade 150 where monitoring the information that may be collected by these tags (i.e., crack formation and propagation, blade tip deflection, strain levels, etc.) might be advantageous. As described, the tag 160 may include a conventional antenna 162 or other conventional means for receiving and transmitting data.

In some cases, the RFID devices may be laminated between outer sheets or layers so that the electronic feature is protected from the conditions within the compressor, as explained in U.S. Pat. No. 7,40,054, which is hereby incorporated in its entirety by reference. Within the compressor, RFID tags 160 may be applied to each of the rotor blades in a stage so that each may be monitored. In other embodiments, only selected blades may be monitored as representative of the overall health of the blades within a particular stage.

A receiver or reader 166 for the RFID system may be suitably provided within the compressor at a distance so that it can read the installed tags on the rotating blades. The reader 166 may be mounted per conventional means to any internal, non-rotating surface of the compressor, such as a position on the inner surface of the casing (not shown). As described above, the reader 166 produces and emits an electromagnetic interrogation field as described above. Preferably, each of the tags 160 uniquely identifies the associated rotor blade 150 so that the reader 166 disposed, for example, on the inner surface of the casing, detects and records during operation, as often as necessary or desirable, each respective tag 160 as it passes and any associated information.

In one example embodiment, the tag 160 and associated antenna 162 may be placed in a position and oriented such that any expected cracks that form would form such that the crack disables the tag 160. An example of this embodiment is the tag 160 of FIG. 4 that is placed near the leading edge 156 of the airfoil 152 at an inner radial location. As shown, the tag 160/antenna 162 of this embodiment may be located such that the expected stretching from the normal crack formation in that particular area of the blade would tear or break or disable the antenna 162 of the RFID tag 160. Made inoperative, the tag 160 will not be detected by the reader 166 as the rotor blade passes. As such, the absence of a signal from the disabled tag 160 or the detecting of a sequential tag signal from the next rotor blade provides an indication to an associated operating system (not pictured) that the particular rotor blade has formed a crack and, further, may be used to suitably trigger an error or defect signal that, in some cases, may cause an appropriate repair action to be taken. Thus, it can be recorded which rotor blade or blades may be damaged and the time of the damage, which may be used for scheduling maintenance, turbine shut down or any other appropriate response.

As one of ordinary skill in the art will appreciate, the operating system may comprise any appropriate high-powered solid-state switching device. The operating system may be a computer; however, this is merely exemplary of an appropriate high-powered control system, which is within the scope of the application. For example, but not by way of limitation, the operating system may include at least one of a silicon controlled rectifier (SCR), a thyristor, MOS-controlled thyristor (MCT) and an insulated gate bipolar transistor. The operating system also may be implemented as a single special purpose integrated circuit, such as ASIC, having a main or central processor section for overall, system-level control, and separate sections dedicated to performing various different specific combinations, functions and other processes under the control of the central processor section. It will be appreciated by those skilled in the art that the operating system also may be implemented using a variety of separate dedicated or programmable integrated or other electronic circuits or devices, such as hardwired electronic or logic circuits including discrete element circuits or programmable logic devices, such as PLDs, PALs, PLAs or the like. The operating system also may be implemented using a suitably programmed general-purpose computer, such as a microprocessor or microcontrol, or other processor device, such as a CPU or MPU, either alone or in conjunction with one or more peripheral data and signal processing devices. In general, any device or similar devices on which a finite state machine capable of implementing the logic described above may be used as the operating system. As shown a distributed processing architecture may be preferred for maximum data/signal processing capability and speed.

Some RFID tags are simply configured to indicate when a particular object bearing the radio frequency identification device (RFID device) passes a detection region of a reader/receiver. Other RFID devices are preprogrammed with non-variable information that can be read by the reader/receiver and provide additional information, (i.e., identifying the object and information related to it, not simply its presence). Still other RFID systems are adapted to include certain read-only (pre-programmed) information and certain rewritable information and/or can have (variable) information selectively inputted thereto. Thus, an RFID tag provided on the rotor blade of a compressor or turbine of a turbine engine may be configured to be selectively disabled, as mentioned above, or more complex electronics may be provided to detect and record other information. As such, the RFID tag can be selectively programmed with this variable blade information and the reader can read the communicated variable information and react as desired. Periodically, after the variable information is read, the RFID tag is preferably reprogrammed with other variable information. The reader disposed on the casing may thus be provided to simply detect the presence of operative RFID tags or may further include a reader to download information wirelessly from the tag.

One such embodiment where the RFID tag 150 is reprogrammed with variable information during use includes a conventional strain gauge 168 that measures the level of strain at the particular location of the rotor blade 150, which is represented in FIG. 4 by the tag 160 and antenna 162 positioned in the approximate mid-area of the suction side of the airfoil 152. In this case, per conventional means, the strain gauge 168 would be coupled to the RFID tag 150 and, at desired intervals, would reprogram the tag 160 with variable information that indicates the current level or reading of the strain gauge 168. This information then may be passed to the reader 166 where it then may be recorded by the operating system (not shown) and acted on accordingly. For example, when the reading of the strain gauge 168 surpasses a certain level, the strain reading may be detected/recorded by the strain gauge 168, programmed into the tag 160, and transmitted to the reader 166/operating system, where a desired alert or warning message may be generated. Such embodiments may include the complex electronics and piezoelectric fibers and the like that are described in U.S. Pat. No. 7,360,996, the entire disclosure of which is hereby incorporated herein by this reference.

Another embodiment where the RFID tag 150 is reprogrammed with variable information during use includes a combined conventional accelerometer/motion sensor 170 that, when taken together, proved a measure of blade tip deflection at that particular location of the rotor blade 150. This particular exemplary embodiment is represented in FIG. 4 by the tag 160 and antenna 162 positioned near the outer radial edge of the suction side of the airfoil 152 near the leading edge 156. In this case, per conventional means, the combined conventional accelerometer/motion sensor 170 would be coupled to the RFID tag 150 and, at desired intervals, would reprogram the tag 160 with variable information that indicates the blade tip deflection at that location. This information then may be passed from the tag 160 to the reader 166 where it then may be recorded by the operating system (not shown) and acted on accordingly. For example, when the blade tip deflection reading surpasses a certain level, the reading may be detected/recorded by the combined conventional accelerometer/motion sensor 170, programmed into the tag 160, and transmitted to the reader 166/operating system, where a desired alert or warning message may be generated. Such embodiments may include the complex electronics and piezoelectric fibers and the like that are described and incorporated above. Other types of sensors also may be coupled with the RFID tag.

From the above description of preferred embodiments of the invention, those skilled in the art will perceive improvements, changes and modifications. Such improvements, changes and modifications within the skill of the art are intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

I claim:

1. A method of monitoring a rotor blade of a turbine engine that includes a plurality of blades mounted to a rotor shaft, comprising:
    a) securing a RFID tag that includes an antenna to at least one of the rotor blades;
    b) securing a RFID reader on a stationary surface on the turbine engine in operational proximity to the RFID tag; and
    c) during operation of the turbine engine, monitoring the RFID tag with the RFID reader;
    wherein the RFID tag is positioned and secured to the rotor blade such that the formation and/or propagation of cracks that are expected to form in the area of the rotor blade on which the RFID tag is positioned and secured disable the RFID tag such that the RFID tag is not readable to the RFID reader.

2. The method according to claim 1, wherein the monitoring the RFID tag with the RFID reader includes at least one of i) detecting whether the RFID tag is operative and ii) reading data from the RFID tag with the RFID reader as the rotor blade on which the RFID tag is secured passes the RFID reader.

3. The method according to claim 2, wherein the RFID tag is positioned and secured to the rotor blade such that the formation and/or propagation of cracks that are expected to form in the area of the rotor blade on which the RFID tag is positioned and secured elongate the RFID tag such that, upon a desired level of elongation, the antenna is broken.

4. The method according to claim 3, wherein the RFID tag is positioned and secured to the rotor blade such that at least a portion of the antenna is substantially perpendicular to the direction of the cracks that are expected to form in the area of the rotor blade on which the RFID tag is positioned and secured.

5. The method according to claim 1, further comprising: d) selectively programming the RFID tag with variable information during operation;
    wherein the monitoring the operation of the RFID tag includes the RFID reader reading the programmed variable information of the RFID tag.

6. The method according to claim 5, further comprising: e) after the reading the programmed variable information, reprogramming the RFID tag with other variable information;
    wherein the reprogramming the RFID tag with other variable information is completed at least in part by a sensor that is connected to the RFID tag.

7. The method according to claim 6, wherein the RFID tag is further preprogrammed with non-variable information which is not affected by subsequent programming and reprogramming pursuant to (d) and (e).

8. The method according to claim 6, wherein the sensor comprises at least one of one of a strain gauge, a motion sensor, and an accelerometer.

9. The method according to claim 1, wherein:
    the rotor blade comprises a compressor rotor blade; and
    the RFID tag comprises a passive RFID tag.

10. A turbine engine comprising:
    a plurality of rotor blades mounted to a shaft;
    a RFID tag that includes an antenna secured to at least a plurality of the rotor blades;
    a RFID reader secured to a stationary surface on the turbine engine in operational proximity to the RFID tag;

wherein the RFID reader is configured to monitor the RFID tags as the RFID tags pass the RFID reader during operation;

wherein the RFID tag is positioned and secured to the rotor blade such that the formation and/or propagation of cracks that are expected to form in the area of the rotor blade on which the RFID tag is positioned and secured disable the RFID tag.

11. The turbine engine of claim 10, wherein the RFID tag uniquely identifies the rotor blade to which it is attached to the RFID reader.

12. The turbine engine of claim 10, wherein the RFID reader is configured to at least one of i) detect whether the RFID tag is operative and ii) read data from the RFID tag with the RFID reader as the rotor blade on which the RFID tag is secured passes the RFID reader.

13. The turbine engine of claim 12, wherein the RFID tag is positioned and secured to the rotor blade such that the formation and/or propagation of cracks that are expected to form in the area of the rotor blade on which the RFID tag is positioned and secured elongate the RFID tag such that, upon a desired level of elongation, the antenna in the RFID tag is broken.

14. The turbine engine of claim 13, wherein the RFID tag is positioned and secured to the rotor blade such that at least a portion of the antenna is substantially perpendicular to the direction of the cracks that are expected to form in the area of the rotor blade on which the RFID tag is positioned and secured.

15. The turbine engine of claim 10, further comprising means for selectively programming the RFID tag with variable information during operation;

wherein the RFID reader is configured to read the programmed variable information of the RFID tag.

16. The turbine engine of claim 15, further comprising means for reprogramming the RFID tag with other variable information after reading the programmed variable information.

17. The turbine engine of claim 15, wherein:
the means for selectively programming the RFID tag with variable information during operation includes a sensor; and
the sensor comprises at least one of one of a strain gauge, a motion sensor, and an accelerometer.

18. The turbine engine of claim 10, wherein:
the rotor blade comprises a compressor rotor blade; and
the RFID tag comprises a passive RFID tag.

* * * * *